United States Patent [19]

Skinner et al.

[11] Patent Number: 5,449,670
[45] Date of Patent: Sep. 12, 1995

[54] COMPOSITION AND METHOD FOR THE TRANSDERMAL DELIVERY OF BIOACTIVE PEPTIDES

[76] Inventors: Wilfred A. Skinner; Kenichiro Saito; Jorge Heller, all of 333 Ravenswood Ave., Menlo Park, Calif. 94025

[21] Appl. No.: 264,760

[22] Filed: Jun. 23, 1994

Related U.S. Application Data

[63] Continuation of Ser. No. 662,976, Feb. 28, 1991, abandoned, which is a continuation of Ser. No. 306,290, Feb. 2, 1989, abandoned, which is a continuation of Ser. No. 824,394, Jan. 23, 1986, abandoned, which is a continuation-in-part of Ser. No. 739,790, May 31, 1985, Pat. No. 4,710,497, which is a continuation-in-part of Ser. No. 729,073, Apr. 30, 1985, abandoned, which is a continuation of Ser. No. 496,732, May 20, 1983, abandoned.

[51] Int. Cl.$^6$ ............................................. A61K 38/16
[52] U.S. Cl. ................................ 514/3; 514/12; 514/947
[58] Field of Search ........................... 514/3, 12, 947

[56] References Cited

U.S. PATENT DOCUMENTS

| | | | |
|---|---|---|---|
| 3,551,554 | 12/1970 | Herschler | 424/128 X |
| 4,039,664 | 8/1977 | Stoughton et al. | 424/180 |
| 4,130,667 | 12/1978 | Smith | 424/361 |
| 4,232,006 | 11/1980 | Taplin et al. | 424/177 |
| 4,405,616 | 9/1983 | Rajadhyaksha | 514/947 X |
| 4,650,351 | 3/1987 | Engle et al. | 400/120 |

*Primary Examiner*—Ronald W. Griffin
*Attorney, Agent, or Firm*—Sughrue, Mion, Zinn, Macpeak & Seas

[57] ABSTRACT

A composition for the transdermal delivery of a biologically active peptide having a molecular weight of about 5,000 or less comprising at lest one biologically active peptide, at least one higher alcohol, ester and/or higher amide in combination with at least one pyrrolidone compound of the formula:

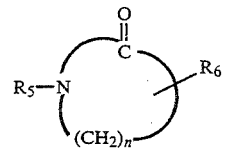

where $R_5$ is hydrogen or a lower alkyl group having 1 to 4 carbon atoms, $R_6$ is hydrogen or a lower alkyl group having 1 to 3 carbon atoms and n is 3, 4 or 5. A method for percutaneously administering such a composition is also disclosed.

25 Claims, No Drawings

COMPOSITION AND METHOD FOR THE TRANSDERMAL DELIVERY OF BIOACTIVE PEPTIDES

CROSS-REFERENCE TO RELATED APPLICATIONS

This is a continuation of prior application Ser. No. 07/662,976 filed Feb. 28, 1991, (abandoned), which is a continuation of prior application Ser. No. 07/306,290 filed Feb. 2, 1989, (abandoned), which is a continuation of prior application Ser. No. 06/824,394 filed Jan. 23, 1986, (abandoned), which is a continuation-in-part of prior application Ser. No. 06/739,790 filed May 31, 1985 (now U.S. Pat. No. 4,710,497), which is a continuation-in-part of prior application Ser. No. 06/729,073 filed Apr. 30, 1985, (abandoned), which is a continuation of prior application Ser. No. 06/496,732 filed May 20, 1983, (abandoned).

FIELD OF THE INVENTION

The present invention relates to a composition and a method for the transdermal delivery of bioactive peptides.

DESCRIPTION OF THE PRIOR ART

The advent of genetic engineering and especially recombinant DNA technology has made available many biologically active peptides that previously were laboratory curiosities. The peptides include human insulin, human growth hormone, bovine growth hormone, endorphins and enkephalines, calcitonin, interferons, interleukins and other lymphokines, TPA, vasopressin, oxytocin and many others.

Peptides are made up of groups of amino acid linked together by amide bonds. The distinction between peptides and proteins which also are groups of amino acids linked by amide bonds is somewhat vague, but usually they are separated by molecular weight or the number of amino acids in the chain. The technology for synthetically producing peptides has been improving as has the technology for producing them biologically via recombinant DNA methods using bacteria.

Use of these biologically active peptides in medical practice is not so simple. Because of the nature of the peptide bond, they are not stable in the acidic conditions of the stomach and thus have very poor oral activity. The most common route of administering biologically active peptides is by the intravenous route which is not amenable to out-patient treatment.

In addition to the acid instability of peptides, enzymes in the body known as peptidases break down these peptides, rapidly destroying their biological activity, some peptides, e.g., Angiotensin I and bradykinin, have a half-life of less than 30 seconds.

Routes other than oral or intravenous administration have thus been studied for the delivery of peptides. Buccal absorption can be accomplished to some extent for some peptides. Rectal absorption has been studied and some delivery of insulin, pentagastrin and gastrin in rats using promoters has been reported. [M. Shichiri et al, J. Pharm. Pharmacol. 30, 806 (1978)] [S. Yoshioka et al, J. Pharm. Sci. 71, 593 (1982)].

Pulmonary absorption has also been studied somewhat and aerosolized insulin was 40% absorbed in rabbits [H. Yoshida et al, J. Pharm. Sci. 68, 670 (1979)].

Recently, nasal absorption has been investigated for peptides. Insulin, LH-RH and vasopressin have been studied in various animal species and in man with some success.

All of the above routes are rather inconvenient for the patient and are still in an experimental stage. A recent article on the subject of delivery of peptides while mentioning the above systems makes no mention of transdermal delivery. [T. Kimara, Pharmacy International (March 1984)].

Bioerodable implants have also been studied as delivery systems for peptides. One disadvantage of such is the difficulty of removal of the drug if side effects arise. This can also be a problem with the other systems mentioned above.

A transdermal delivery system for peptides would be ideal in many ways. A search of the literature indicated no reports of successful transdermal delivery of peptides.

In a classical review paper on percutaneous absorption, Idson mentions that

> [A]n inverse relationship appears to exist between absorption rate and molecular weight. High molecular weight materials also show variable penetration. Very large molecules such as proteins and polysaccharides went through (the skin) very poorly, if at all.

The use of dimethyl sulfoxide as a penetration carrier indicated that substances having molecular weight of 3,000 or more cannot be transported into the skin. [A. Kappert, Schweiz. Med. Wockenschr., 98, 1829 (1968)]. Substances having molecular weights of 3,000 or more cannot be transported into the stratum corneum using conventional vehicles such as DMSO. [J. Ostrenga et al, J. Pharm. Sci., 60, 1175 (1971)].

SUMMARY OF THE INVENTION

Transdermal delivery of peptides of varying molecular weight below about 5,000, preferably below about 4,000, and most preferably below about 3,000, which may have various amino acid compositions, has been attained by the use of topical ointments, gels or devices using unique vehicle combinations comprising one or more conditioners and one or more promoters.

The conditioners include alcohols, esters and/or amides and the promoter is a pyrrolidone.

DESCRIPTION OF THE PREFERRED EMBODIMENTS

As conditioners, the esters are alcohol esters of aliphatic carboxylic acids having a total number of carbon atoms of from 7 to 18, preferably 7 to 17. Mixtures thereof can also be used As the alcohol moiety, monovalent alcohols having 1 to 6 carbon atoms such as methyl alcohol, ethyl alcohol, n-propyl alcohol, iso-propyl alcohol, n-butyl alcohol, iso-butyl alcohol, sec-butyl alcohol, t-butyl alcohol, n-amyl alcohol, iso-amyl alcohol, n-hexyl alcohol, etc., are preferred. Further, as the carboxylic acid moiety, fatty acids having 6 to 16 carbon atoms are preferred and saturated fatty acids having 8 to 14 carbon atoms are most preferred. Specific examples of such esters include methyl laurate, ethyl laurate, butyl laurate, iso-propyl myristate, etc.

The amide conditioners can be represented by the formula:

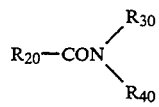

where $R_{20}$ is a $C_5$ to $C_{17}$ alkyl group, more preferably a $C_7$ to $C_{13}$ alkyl group and $R_{30}$ and $R_{40}$, which may be the same or different, can be hydrogen or a $C_1$ to $C_3$ alkyl group. Mixtures thereof can also be used.

The conditioner of the present invention can also be a higher aliphatic monoalcohol or a mixture of higher aliphatic monoalcohols having from 8 to 24 carbon atoms. The higher aliphatic monoalcohol can be branched, straight chain, saturated, unsaturated or cyclic and may be primary, secondary or tertiary subject to the following restrictions regarding melting point. Any higher aliphatic monoalcohol used must have a melting point below 38° C.; accordingly, any higher aliphatic monoalcohol containing more than 14 carbon atoms must contain at least one unsaturated bond, at least one branched chain and/or at least one alicyclic group in the molecule thereof.

The terminology "at least one" reflects the fact that, if desired, the higher aliphatic monoalcohol containing more than 14 carbon atoms can simultaneously meet two or three of these criteria.

Generally no more than about four or five unsaturated bonds, i.e., a carbon-carbon unsaturated bond, will be present in such a higher aliphatic monoalcohol, though this is not limitative. Further, while the at least one unsaturated bond is most preferably present in the main chain of the higher aliphatic monoalcohol, it can be present in a branched chain when a branched chain is present or in an alicyclic moiety when an alicyclic moiety is present.

The branched chain must contain at least one carbon atom, i.e., can be methyl. Typically, however, the branched chain will contain no more than about 13 carbon atoms in which, for a 26 carbon atom higher aliphatic monoalcohol, the branch and the main chain will have the same number of carbon atoms. The branched chain can contain the at least one unsaturated bond as above discussed and/or can contain the alicyclic moiety as now discussed.

Higher aliphatic monoalcohols containing more than 14 carbon atoms can also contain at least one alicyclic moiety which must be a non-aromatic ring. The alicyclic moiety must contain at least 3 carbon atoms and generally will contain no more than 12 carbon atoms. It is possible that more than one alicyclic moiety can be present, if desired, and, as earlier indicated, the alicyclic moiety, for example, a cyclohexyl group, can contain at least one unsaturated bond and may have at least one branched chain substituted thereon. The alicyclic group can be in the main or branched chain of the alcohol or substituted thereon.

In summary, the requirement that a higher aliphatic monoalcohol useful per the present invention which contains more than 14 carbon atoms must contain at least one unsaturated bond, at least one branched chain and/or at least one alicyclic group in the molecule thereof can be met by any of the above possibilities and it is to be understood that the at least one unsaturated bond and the at least one alicyclic group may be, but need not be, in the main chain of the higher aliphatic monoalcohol.

It is our current belief that mixtures of alcohols, esters and/or amides should also be useful to form conditioner systems per the present invention in combination with a pyrrolidone. Currently, however, we see no special benefit to using a mixture of various classes of conditioners.

The promoters are represented by the general formula:

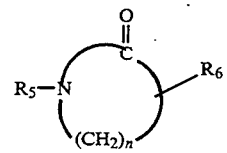

wherein $R_5$ represents a hydrogen atom or a lower alkyl group having 1 to 4 carbon atoms (methyl, ethyl, n-propyl, iso-propyl, etc.), $R_6$ represents a hydrogen atom or a lower alkyl group having 1 to 4 carbon atoms and n represents an integer of 3 to 5.

Specific examples thereof include 2-pyrrolidone, N-methylpyrrolidone, N-methylpiperidone, caprolactam, N-methylcaprolactam, etc.

The fatty acid esters are conveniently represented by the formula $R_1COOR_2$, $R_1$ representing the acid moiety and $R_2$ representing the alcohol moiety. It is most preferred that the total number of carbon atoms in $R_1$ and $R_2$ be from 10 to 17.

$R_1$ and $R_2$ may be linear, branched, saturated, unsaturated or aromatic.

The pyrrolidones are most preferably alkyl pyrrolidones of the formula:

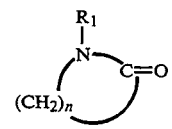

where $R_1$ is an alkyl group containing up to 4 carbon atoms and n is 3 to 5.

We consider the materials such as the pyrrolidone compounds to basically serve a promoter function and materials such as the alcohols, esters and amides to serve as conditioners which enhance the function of the promoter. We further believe that the promoters carry the active agent whereas the conditioners open up the stratum corneum. We do not wish to be bound by these theories, and we merely use the terminology "promoter" and "conditioner" to maintain a line of distinction between the two classes of materials which are mandatorily used in combination.

The base compositions of the present invention can be prepared by homogeneously dissolving the pyrrolidone compound(s) in the alcohol(s), ester(s) or amide(s) or vice-versa. The amount of the alcohol(s), ester(s) or amide(s) to be used is generally from 0.1 to 80% by weight based on the total weight of the pyrollidone compound(s), the alcohol(s), ester(s) and amide(s), preferably 0.5 to 50% by weight. Of course, pharmaceutically acceptable additives such as water, etc., can also be added to the base compositions.

The pharmaceutical compositions for topical application per the present invention can be prepared by blending bioactive peptides with the above described base compositions. There is no particular limit on the bioactive peptides used so long as they are systemically active, percutaneously applicable and have a molecular weight less than about 5,000.

The amount of biologically active peptide(s) blended is sufficient if it is effective for achieving the desired pharmaceutical effect, which varies depending upon the kind of peptide(s), body weight of the patient, symptoms, etc. The amount may thus be suitably chosen depending upon these conditions. In general, it is preferred that the peptide(s) be employed in an amount of 0.01 to 50% by weight, more preferably 0.05 to 10% by weight, based on the total weight of the conditioner and promoter.

The dose of the peptide(s) administered can be controlled by increasing or decreasing the amount of peptide(s) and/or the area of skin to which the pharmaceutical compositions are applied. Accordingly, the amount of the peptide(s) is not necessarily limited to the above described ones.

As will be apparent to one skilled in the art, with increasing concentrations of peptide(s) increasing amounts of peptide(s) will be absorbed by the subject. The following discussion is given in terms of blood levels of peptide(s) (ng/ml of plasma), this being dependent upon the total area of dermal application, as there is a substantially linear increase in amount of peptide(s) absorbed with area.

For a constant area of application and a constant absolute amount of adjuvant, the blood level of the peptide(s) at any given time is a function of the concentration of peptide(s) in the composition. That is, increased concentrations of peptide(s) in the formulation result in more rapid peptide(s) penetration and higher blood levels.

A further factor which must be considered is that the amount of peptide(s) absorbed will depend on the site of application, for example, scalp, ventral forearm, behind the ear, chest, etc. Typically, an area rich in blood vessels is selected.

For most applications, the concentration of peptide(s) will generally be on the order of 0.01 to 50% based on the weight of the conditioner and promoter, the amount of total composition applied will be about 0.1 mg to 100 mg per cm$^2$ and the total area of application will be on the order of about 0.5 cm$^2$ to about 100 cm$^2$, which will provide therapeutic blood levels of the desired peptide(s).

These ranges are not, however, to be considered as limitative.

In general, the rate of transepidermal peptide(s) absorption will depend upon the factors previously discussed (nature and amount of conditioner/promoter, concentration of peptide(s) in the formulation, and surface area of skin application). Thus, peak blood levels of the peptide(s) may be reached more slowly and will reach about the same level as those obtained by intravenous administration. Alternatively, the blood level of peptide(s) attained by single dose intra-venous administration may be maintained for an extended period by subsequent percutaneous administration of the peptide(s). In the latter case, the initial intra-venous dose may be smaller than the normal therapeutic intravenous dose so that side effects associated with higher-than-optimal therapeutic blood levels attained by a reduced intra-venous dose may be maintained by the subsequent transepidermal administration at a proper rate.

The method of the present invention finds application with living mammals in general, most particularly man and domestic animals such as cows, sheep, horses, dogs, cats and the like.

The pharmaceutical composition of the present invention is administered to the outer skin as a simple mixture or as a medical preparation by adding known pharmaceutically acceptable third component in the form of solutions, ointments (paste—including creams and gels) lotions, adhesive tapes, a plaster, etc.

For example, solutions may simply comprise the peptide(s) dissolved in the conditioner/promoter with optional components, e.g., glycerin, and the solutions may be incorporated into absorbents, e.g., a gauze, porous membrane, etc.

Ointments, gels or creams may contain conventional ingredients (e.g., polyethylene glycol and hydroxy propylcellulose, etc.) to form the same, and the same may be spread onto backing materials, e.g., a plastic film.

Similarly, plasters or adhesive tapes may contain the peptide(s) and conditioner/promoter in an adhesive base, e.g., acrylic copolymers or other synthetic gums.

The composition of the present invention (peptide(s)-/conditioner(s)/promoter(s)) may be added to such a composition in varying amounts as desired, generally from 10 to 99% by weight of the total formulation.

In developing the present invention, we had used diffusion cells. The diffusion cells method provides a qualitative assessment of the active effect on percutaneous absorption peptide(s) using a conditioner/promoter system per the present invention.

Rat full thickness skins were used in the following diffusion cell method.

The skin was excised form the shaved abdominal site of deceased male albino rats weighting 150~300 g and washed with normal saline solution after the subpercutaneous fat was carefully removed with scissors.

The diffusion cell method of Michaels, AIChEb Journal, 21, [5], pp. 985–996 (1975) was followed. The rat skin was mounted vertically in a diffusion cell apparatus; the exposed area of the skin approximated 4.15 cm$^2$.

The active agent/vehicle solution of known concentration was added to the donor side compartment of the cell, which was exposed to the epithelial side of the skin and a normal saline solution was placed in the receptor side compartment.

The penetration rate was studied in a thermostated bath at 30° C. At appropriate intervals samples were withdrawn from the receptor side compartment and subsequently analyzed for active agent concentration by standard analytical methods.

Unless otherwise indicated, all peptide flux levels were determined by radioimmunoassay in a conventional manner using commercially available materials in kit form namely:

Angiotensin I-from:
  New England Nuclear 549 Albany Street Boston, Mass. 02118
  RAINEN TM Angiotensin I [$^{125}$] RIA Kit;
Glucagon-from:
  Cambridge Medical Diagnostics, Inc. 575 Middlesex Turnpike Billerica, Mass. 01865

Glucagon has a molecular weight of approximately 3,550.

I Glucagon Radioimmunioassay Kit.

The data obtained clearly show the synergistic effect of the conditioner/promoter systems of the present invention on peptide flux as compared to the use of a conditioner alone or a promoter alone is consistently seen throughout the EXAMPLES where all percents are volume percents based on the total volume of the conditioner/promoter unless otherwise indicated.

EXAMPLE 1

Angiotensin I (human)—10 amino acids—was the biologically active peptide selected. It had a molecular weight of about 1,200. 1 mg of Angiotensin I in 1 ml of the vehicle was used in the diffusion cell (donor side). The results for various conditioners/promoters and for several controls are set forth in the Table below.

TABLE

| 25% | 75% | ng/Angiotensin I/cm²/6 hrs. |
|---|---|---|
| 3-octanol | NMP* | 114 |
| linalool | NMP | 214 |
| 1-dodecanol | N-methyl caprolactone | 65 |
| Oleyl alcohol | NMP | 137 |
| Phytol | NMP | 100 |
| Ethyl laurate | NMP | 178 |
| Isopropyl myristate | NMP | 70 |
| (Controls) | | 4.6 |
| NMP (100%) | | |
| 3-Octanol (100%) | | 1.1 |
| Linalool (100%) | | 2.2 |
| 1-dodecanol (100%) | | 1.2 |
| Oleyl alcohol (100%) | | 2.1 |
| Ethyl laurate (100%) | | 0.5 |
| Isopropyl myristate (100%) | | 3.3 |

*NMP is the abbreviation for N-methyl pyrrolidone.

EXAMPLE 2

The procedure of EXAMPLE 1 was followed with various vehicle systems. One mg of Angiotensin I (human) in 1 ml of the promoter/conditioner was used in the donor side compartment of the cell, unless otherwise indicated. The results are set forth below.

| Vehicle | ng Angiotensin I/cm²/6 hrs. |
|---|---|
| 5% linalool, 95% NMP | 80 |
| 10% linalool, 90% NMP | 107 |
| 50% linalool, 50% NMP | 76 |
| 5% 1-dodecanol, 95% NMP | 112 |
| 10% 1-dodecanol, 90% NMP | 116 |
| 50% 1-dodecanol, 50% NMP | 121 |
| 25% 1-dodecanol, 75% NMP | 181 |
| 5 mg Angiotensin I per each 1 ml 1-dodecanol and NMP (hereafter the same) | |
| 25% 1-dodecanol, 75% NMP/ glycerol (2 vol. pts. NMP/ 1 vol. pt. glycerol | 72 |
| 25% 1-dodecanol, 75% NMP with 0.5 mg isosorbide dinitrate per each 1 ml thereof | 96 |
| 5% methyl salicylate based, on volume of 25% 1-dodecanol and 75% NMP | 132 |
| 10% methyl salicylate based on volume of 25% 1-dodecanol and 75%.NMP | 154 |
| 25% N,N-dimethyldodecamide | 380 |

EXAMPLE 3

The procedure of EXAMPLE 1 was followed except for using 1 mg of glucagon in 1 ml of the promoter/conditioner (total was 1 ml) in the donor side compartment of the cell. Glucagon comprises 29 amino acids and has a molecular weight of about 3,500. The results are set forth below.

| Vehicle | ng Glucagon/cm²/ 6 hrs. |
|---|---|
| 25% oleyl alcohol, 75% NMP | 2.5 |
| 25% linalool, 75% NMP | 3.0 |
| 25% N,N-dimethyldodecamide, 75% NMP | 285 |
| 25% 1-dodecanol, 75% NMP | 2.9 |
| 25% 1-dodecanol, 75% NMP + 0.5 mg/ml isosorbide dinitrate per ml thereof | 4.0 |
| 25% 1-dodecanol, 75% NMP + 5% methyl salicylate based on 1-dodecanol and NMP | 6.2 |

EXAMPLE 4

The procedure of Example 3 was followed except for using 1 mg of luteinizing hormone—releasing hormone (LHRH) per ml of the promoter/conditioner in the donor side compartment of the diffusion cell.

The flux of LHRH was determined by the HPLC method.

LHRH comprises 10 amino acids.

| Vehicle | ng LHRH/cm²/6 hrs. |
|---|---|
| 25% oleyl alcohol, 75% NMP | 2,600 |
| 25% linalool, 75% NMP | 3,000 |
| 25% ethyl laurate, 75% NMP | 5,000 |
| 25% N,N-dimethyldodecamide, 75% NMP | 60,900 |
| 25% 1-dodecanol, 75% NMP | 12,600 |
| 25% 1-dodecanol, 75% NMP with 0.5 mg isosorbide dinitrate per 1 ml thereof | 10,100 |
| 5% methyl salicylate based on volume of 25% 1-dodecanol and 75% NMP | 10,200 |

While there have been described what are at present considered to be the preferred embodiments of this invention, it will be obvious to those skilled in the art that various changes and modifications can be made therein without departing from the invention, and it is, therefore, intended to cover all such changes and modifications as fall within the true spirit and scope of the invention.

What is claimed is:

1. A composition for the transdermal delivery of a biologically active peptide having a molecular weight of below about 4,000 consisting essentially of at least one biologically active peptide having a molecular weight of below about 4,000, at least one higher alcohol having a melting point below 38° C., ester and/or higher amide in combination with at least one pyrrolidone compound of the formula:

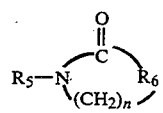

where $R_5$ is hydrogen or a lower alkyl group having 1 to 4 carbon atoms, $R_6$ is hydrogen or a lower alkyl group having 1 to 3 carbon atoms and n is 3 or 4.

2. The composition of claim 1, wherein the ester is an alcohol ester of an aliphatic carboxylic acid having a total number of carbon atoms of from 7 to 18, the higher amide has the formula:

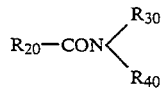

where $R_{20}$ is a $C_5$ to $C_{17}$ alkyl group, and $R_{30}$ and $R_{40}$, which may be the same or different, can be hydrogen or a $C_1$ to $C_3$ alkyl group, and the higher alcohol is a higher aliphatic monoalcohol having from 8 to 24 carbon atoms.

3. The composition of claim 3, wherein said at least one higher alcohol, ester and/or higher amide is selected from the group consisting of 3-octanol, linalool, 1-dodecanol, oleyl alcohol, phytol, ethyl laurate, isopropyl, myristate, methyl salicylate and N,N-dimethyldodecamide and the at least one pyrrolidone compound is selected from the group consisting of N-methyl pyrrolidone and N-methyl caprolactone.

4. The composition of claim 1, wherein the at least one higher aliphatic monoalcohol is used.

5. The composition of claim 1, wherein the at least one ester is used.

6. The composition of claim 5, wherein the alcohol in the ester is a monovalent alcohol having 1 to 6 carbon atoms and the aliphatic carboxylic acid in the ester is a fatty acid 6 to 16 carbon atoms.

7. The composition of claim 1, wherein the at least one higher amide is used.

8. The composition of claim 1, wherein the biologically active peptide is selected from the group consisting of glucagon and luteinizing hormone-releasing hormone.

9. The composition of claim 1, wherein the amount of the at least one higher alcohol, ester and/or higher amide is from 0.1 to 80% by weight based on the total weight of the at least one higher alcohol, ester and/or higher amide and the at least one pyrrolidone compound, and the amount of the at least one biologically active peptide is from 0.01 to 50% by weight based on the total weight of the at least one higher alcohol, ester and/or higher amide and the at least one pyrrolidone compound.

10. The composition of claim 1, wherein the biologically active peptide has a molecular weight of below about 3,000 or less.

11. A composition for the transdermal delivery of a biologically active peptide which consists essentially of at least one biologically active peptide having a molecular weight of below about 4,000 or less, at least one higher alcohol having a melting point below 38° C., and higher amide in combination with at least one pyrrolidone compound of the formula:

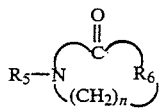

where $R_5$ is hydrogen or a lower alkyl group having 1 to 4 carbon atoms, $R_6$ is hydrogen or a lower alkyl group having 1 to 3 carbon atoms and n is 3, 4 or 5.

12. The composition of claim 11, wherein the biologically active peptide has a molecular weight of below about 3,500.

13. The composition of claim 11, wherein the biologically active peptide is glucagon.

14. The composition of claim 11, wherein the biologically active peptide is luteinizing hormone-releasing hormone.

15. A composition for the transdermal delivery of a biologically active peptide having a molecular weight of below about 3,550 consisting essentially of at least one biologically active peptide having a molecular weight of below about 3,550, at least one higher alcohol having a melting point below 38° C., ester and/or higher amide in combination with at least one pyrrolidone compound of the formula:

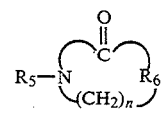

where $R_5$ is hydrogen or a lower alkyl group having 1 to 4 carbon atoms, $R_6$ is hydrogen or a lower alkyl group having 1 to 3 carbon atoms and n is 3 or 4.

16. A method for percutaneously administering at least one biologically active peptide to a living mammal which comprises applying the at least one biologically active peptide having a molecular weight of below about 4,000 to the skin of the living mammal in a mixture which comprises:
(A) at least one higher alcohol having a melting point below 38° C., ester and/or amide and
(B) one or more pyrrolidone compounds of the formula:

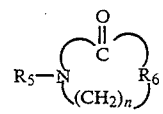

where $R_5$ is hydrogen or a lower alkyl group having 1 to 4 carbon atoms, $R_6$ is hydrogen or a lower alkyl group having 1 to 3 carbon atoms and n is 3 or 4.

17. The method of claim 16, wherein the ester is an alcohol ester of an aliphatic carboxylic acid having a total number of carbon atoms of from 7 to 18, the higher amide has the formula:

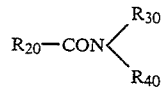

where $R_{20}$ is a $C_5$ to $C_{17}$ alkyl group, and $R_{30}$ and $R_{40}$, which may be the same or different, can be hydrogen or a $C_1$ to $C_3$ alkyl group, and the higher alcohol is a higher aliphatic monoalcohol having from 8 to 24 carbon atoms.

18. The method of claim 17, wherein the at least one higher aliphatic monoalcohol is used.

19. The method of claim 17, wherein the at least one ester is used.

20. The method of claim 17, wherein the at least one higher amide is used.

21. The method of claim 17, wherein the alcohol in the ester is a monovalent alcohol having 1 to 6 carbon atoms and the aliphatic carboxylic acid in the ester is a fatty acid having 6 to 16 carbon atoms.

22. The method of claim 17, wherein the biologically active peptide is selected from the group consisting of glucagon and luteinizing hormone-releasing hormone.

23. The method of claim 17, wherein said at least one higher alcohol, ester and/or higher amide is selected from the group consisting of 3-octanol, linalool, 1-dodecanol, oleyl alcohol, phytol, ethyl laurate, isopropyl myristate, methyl salicylate and N,N-dimethyldodecamide and the at least one pyrrolidone compound is selected from the group consisting of N-methyl pyrrolidone and N-methyl caprolactone.

24. The method of claim 16, wherein the amount of the at least one higher alcohol, ester and/or higher amide is from 0.1 to 80% by weight based on the total weight of the at least one higher alcohol, ester and/or higher amide and the at least one pyrrolidone compound, and the amount of the at least one biologically active peptide is from 0.01 to 50% by weight based on the total weight of the at least one higher alcohol, ester and/or higher amide and the at least one pyrrolidone compound.

25. A method for percutaneously administering at least one biologically active peptide to a living mammal which comprises applying the at least one biologically active peptide having a molecular weight of below about 3,550 to the skin of the living mammal in a mixture which comprises:
(A) at least one higher alcohol having a melting point below 38° C., ester and/or amide and
(B) one or more pyrrolidone compounds of the formula:

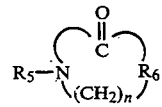

where $R_5$ is hydrogen or a lower alkyl group having 1 to 4 carbon atoms, $R_6$ is hydrogen or a lower alkyl group having 1 to 3 carbon atoms and n is 3 or 4.

* * * * *